US010988396B2

(12) United States Patent
Creech et al.

(10) Patent No.: US 10,988,396 B2
(45) Date of Patent: Apr. 27, 2021

(54) METHOD AND APPARATUS FOR ANAEROBIC SLUDGE DIGESTION MIXING AND HEAT EXCHANGE

(71) Applicant: Chicago Bridge & Iron Co., Plainfield, IL (US)

(72) Inventors: David Thomas Creech, Plainfield, IL (US); Koray Kuscu, Plainfield, IL (US); Chelsea Erin LaHaye, Plainfield, IL (US); Stephen Hsu, Plainfield, IL (US)

(73) Assignee: Chicago Bridge & Iron Co., Plainfield, IL (US)

( * ) Notice: Subject to any disclaimer, the term of this patent is extended or adjusted under 35 U.S.C. 154(b) by 112 days.

(21) Appl. No.: 16/376,651

(22) Filed: Apr. 5, 2019

(65) Prior Publication Data

US 2019/0337828 A1  Nov. 7, 2019

Related U.S. Application Data

(60) Provisional application No. 62/653,839, filed on Apr. 6, 2018.

(51) Int. Cl.
*C02F 3/00* (2006.01)
*C02F 3/12* (2006.01)
*C02F 3/20* (2006.01)

(52) U.S. Cl.
CPC ............ *C02F 3/1252* (2013.01); *C02F 3/201* (2013.01); *C02F 3/205* (2013.01); *C02F 2203/006* (2013.01)

(58) Field of Classification Search
None
See application file for complete search history.

(56) References Cited

U.S. PATENT DOCUMENTS

| 923,571 A | 6/1909 | Paterson |
|---|---|---|
| 1,722,945 A | 7/1929 | Pruss |
| 2,577,797 A | 12/1951 | Moyer |

(Continued)

FOREIGN PATENT DOCUMENTS

| CA | 3036743 A1 | 3/2018 |
|---|---|---|
| CN | 101643273 A | 2/2010 |

(Continued)

OTHER PUBLICATIONS

Partial English machine translation of DE 10 2010 031860 (Year: 2020).*

(Continued)

*Primary Examiner* — Chester T Barry
(74) *Attorney, Agent, or Firm* — Osha Bergman Watanabe & Burton LLP

(57) ABSTRACT

The embodiments herein disclose a method and apparatus for mixing sludge retained in a digester. A jet nozzle assembly for mixing contents of a vessel is used. The jet nozzle assembly having a central outlet pipe terminating at a jet nozzle, a low pressure nozzle assembly disposed concentrically about the central outlet pipe, the low pressure nozzle having a plurality of openings disposed circumferentially about the low pressure nozzle assembly. The plurality of openings are an axial distance from the outlet jet nozzle.

25 Claims, 6 Drawing Sheets

(56) References Cited

U.S. PATENT DOCUMENTS

| | | | |
|---|---|---|---|
| 4,401,565 A * | 8/1983 | Schimel | C02F 3/286 |
| | | | 210/258 |
| 5,409,610 A | 4/1995 | Clark | |
| 5,564,825 A | 10/1996 | Burt | |
| 5,658,076 A | 8/1997 | Crump et al. | |
| 5,735,600 A | 4/1998 | Wyness et al. | |
| 5,942,116 A * | 8/1999 | Clark | C02F 3/2873 |
| | | | 210/194 |
| 6,012,020 A | 1/2000 | Gardell et al. | |
| 7,913,351 B2 * | 3/2011 | Moriya | H01L 21/67069 |
| | | | 15/320 |
| 8,118,477 B2 | 2/2012 | Lamon | |
| 8,162,531 B2 | 4/2012 | Crump | |
| 8,924,167 B2 | 12/2014 | Decker | |
| 8,931,948 B2 | 1/2015 | Coy | |
| 2011/0180152 A1 | 7/2011 | Dorsch | |
| 2011/0263407 A1 * | 10/2011 | Jew | C02F 11/127 |
| | | | 494/6 |

FOREIGN PATENT DOCUMENTS

| | | |
|---|---|---|
| DE | 102010031860 A1 | 1/2012 |
| EP | 1574482 A1 | 9/2005 |

OTHER PUBLICATIONS

Extended European Search Report issued in corresponding European Application No. 19167335.9 dated Jul. 9, 2019 (20 pages).
Office Action issued in corresponding European Application No. 19167335.9, dated Nov. 11, 2020 (7 pages).

* cited by examiner

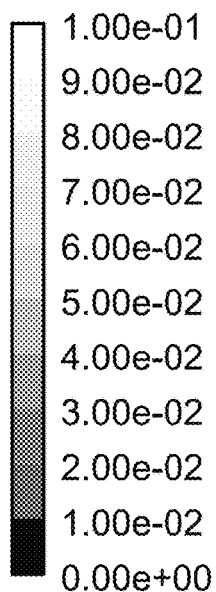
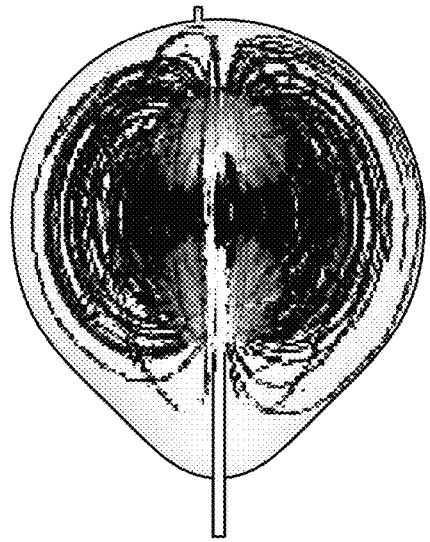
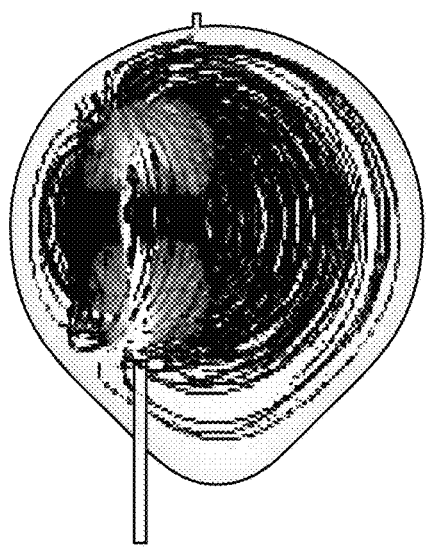
FIG. 6A                    FIG. 6B
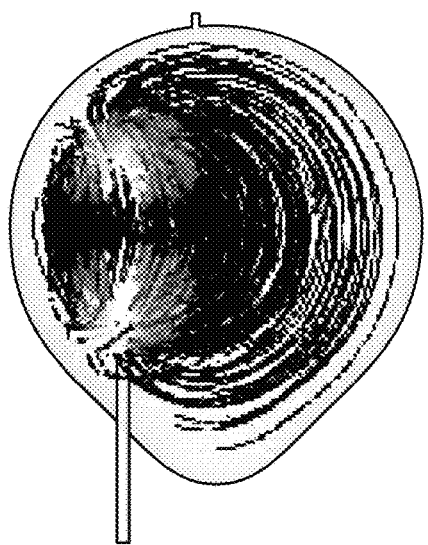
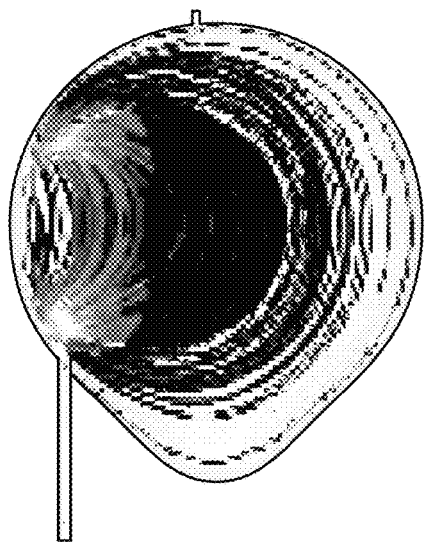
FIG. 6C                    FIG. 6D

METHOD AND APPARATUS FOR ANAEROBIC SLUDGE DIGESTION MIXING AND HEAT EXCHANGE

FIELD OF THE DISCLOSURE

Embodiments disclosed herein relate to systems and processes for anaerobic digestion of biosolids retained in a digester. More particularly, embodiments disclosed herein relate to a jet nozzle assembly for more efficient mixing of the biosolids circulated through a digester.

BACKGROUND OF INVENTION

Historically, anaerobic sludge digestion has been used for stabilization of primary clarifier sludge. More recently, it has been applied to various biological sludge formations and sludge mixtures containing significant industrial waste contributions. Anaerobic digestion is a collection of processes by which microorganisms break down biodegradable material in the absence of oxygen.

Wastewater treatment plants produce large volumes of biosolids that are settled, floated, or produced in the plant during the process of purification of the wastewater that enters the plants. The solids (sludge) must be processed to meet stringent standards prior to discharge into the natural environment. As used herein, the terms biosolids, solids, digesting sludge, sludge, and liquid sludge are used interchangeably to refer to the contents retained in a digester for undergoing anaerobic digestion. Sludge anaerobic digestion is one of the most efficient means for stabilizing the biosolids found in wastewater treatment plants and other types of plants that handle organic materials for ultimate disposal or re-use. In addition, anaerobic digestion has an additional benefit in that the digestion processes produce fuel known as biogas as a naturally occurring part of the digestion process. This emitted biogas, also known as digester gas, once collected, may be reused for various other purposes. For example, digester gas is often used as fuel for engines and turbines that are used to drive equipment or may also be used to produce electricity.

Digesters are the vessels used for retaining sludge (biosolids) for purposes of managed anaerobic digestion and collection of the gas produced from the digesting biosolids. For many years, a digester when found at an industrial site tended to be a cylindrically-shaped vessel, also known as silo shaped. Lately, more sites are using what are known as Egg-Shaped Digesters (ESDs), which are considered to provide greater mixing capabilities by virtue of their shape. Most ESDs include some degree of sloping of the sides, and have a circular or spherical middle section, with some conical sections being located either at the top or bottom of the digester, or both.

Anaerobic biosolids degradation requires proper mixing and effective temperature control to be properly managed. Anaerobic digestion involves a complex microbiological community in which various groups of organisms carry our initial, intermediate, and final stabilization steps. The groups of organisms work together in a symbiotic relationship. Not only is a constant temperature important but the food supply should be available on a steady state basis. This requires that the material within the digester be well mixed. Proper and effective mixing is also necessary because stagnation of material within the anaerobic digester can create process and operational problems. When material stagnates either at the top surface or at the vessel bottom, the digestion process slows substantially, reducing the amount of solids degradation and gas production. ESDs have a natural mixing advantage by eliminating the corners found on cylindrically-shaped vessels, which tend to form stagnant zones. Nevertheless, additional systems are necessary and implemented to mix the sludge and prevent stagnation. Most digesters are mixed in a turbulent manner, usually by generating a high-velocity flow that entrains surrounding fluid which is mixed primarily by the mechanism of turbulent diffusion.

Mixing performance in digesters is measured indirectly by a number of means, including digester volume turnover time, which is the vessel volume divided by the mixing pump flow rate, and unit power, which is mixing pump power divided by vessel volume. These ratios are used with rules-of-thumb to size mixing systems in digesters. However, they fail to differentiate between the effects that mixing flow patterns in the digester have on mixing performance. An alternative to indirect methods is the Coefficient of Variation (COV). The COV is a spatial measurement of mixing that indicates how homogeneous a fluid is at a particular time. The COV is defined as the standard deviation of concentration measurements divided by the mean concentration, and is often expressed as a percentage. The COV can be measured in computational fluid dynamics analysis or experiment by injecting tracer at the digester sludge inlet and measuring tracer concentration at a number of different locations in the digester. It is generally accepted in the industry that 10% COV represents complete mixing in a digester, though acceptable volatile solids reduction and gas production may be achieved at higher values of COV. By performing these measurements at various times after injection of the tracer the time to reach a target COV and the time to reach the steady state COV can be determined. A well-designed mixing system can achieve the target COV with less equipment, less pump power for a lower installed cost and lower operational cost and in less time. Another method to quantify mixing is by a residence time distribution (RTD). The RTD is a temporal measurement of mixing that describes how long particles injected into the digester will remain. In an actual digester particles injected at the same time will have a range of residence times, so the statistical distribution of residence times is necessary to characterize temporal mixing. As for the COV, the RTD can be measured in analysis or experiment by injecting tracer at the digester sludge inlet and measuring tracer concentration over time at the digester sludge drain. The residence time has practical meaning for digesters because the processing of biosolids by anaerobic digestion requires time, and the "volatile solids reduction" of biosolids by anaerobic digestion is correlated to the mean of the residence time distribution. A minimum value for the mean RTD is commonly specified by the purchasers of digesters and by regulatory authorities. A well-designed mixing system will maximize RTD.

Many existing digesters, including ESDs, utilize pumped mixing systems, where the pumps are located outside of the vessel. Pumped mixing systems typically have lower maintenance cost than mechanical mixers, which have moving equipment inside the vessel and can require seals where shafts penetrate the vessel. Often these pumped mixing systems incorporate multiple nozzles and a single low pressure nozzle at the side of the vessel to recirculate the vessel contents through the pump. Pumped mixing systems work by entraining surrounding fluid into a turbulent jet. Some pumped mixing systems incorporate draft tubes which utilize the Venturi effect to entrain fluid into the draft tube where it then mixes. Some draft tube systems incorporate nozzles at top and bottom of the draft tube and by closing and opening valves are operated sequentially in up mode, the flow is directed through the bottom nozzle upwards through the draft tube, followed by down mode, where the flow is directed through the top nozzle downwards through the draft tube. Some pumped mixing systems utilize free jets to entrain surrounding fluid. The mixing performance of each of these mixing systems can be quantified by the COV.

Existing pumped mixing systems have several drawbacks. The cost of the nozzles, draft tubes and piping required by these systems is high. It is difficult to locate and orient the nozzles in the optimal manner for mixing. To make up for suboptimal flow patterns higher pump flow rates are required, increasing the cost of equipment and operating costs. For systems with multiple flow modes the operational complexity is increased. If the cycle time for these modes is less than the time to reach the target COV then mixing may be inadequate. This increases the burden on the digester operator and the likelihood that the mixing system will be operated in a sub-optimal manner.

Another important issue in digester mixing is the handling of sediment, and in particular sediment containing heavy abrasive materials such as sand. This sediment is often referred to as grit. Grit that flows through the mixing system can accelerate wear. However, the remainder of sediment includes biosolids, which must be well mixed to allow break down through anaerobic digestion. Therefore, in digesters where there is a significant amount of heavy grit in the sludge it is advantageous to prevent the heavy grit from entering the mixing system, while still mixing biosolids, and allowing the heavy grit to settle to the bottom of the digester, where it can be flushed from the digester. Some existing digesters have nozzles for flushing sediment from the bottom, but existing mixing systems do not have a means to design for the settlement of heavy grit or to sense when sediment accumulates on the bottom of the digester. Some digesters have been known to accumulate large amounts of sediment which was only discovered when the vessel was emptied for maintenance. This accumulation reduces the operating volume of the vessel, which can lead to insufficient volatile solids reduction.

SUMMARY OF THE DISCLOSURE

Digesters useful in anaerobic digestion of liquid sludge, i.e biosolids, located therein, using draft tubes with jet nozzles have drawbacks including complicated flow schemes and operation, as well as mixing inefficiencies. Embodiments disclosed herein are directed toward mixing systems that are simpler and provide better mixing than draft tubes. Furthermore, it has been found that the jet nozzle assembly located centrally in the digester is beneficial in achieving proper mixing of the contents.

BRIEF DESCRIPTION OF DRAWINGS

FIGS. 6A-D illustrate flow patterns for an ESD with varying offset.

DETAILED DESCRIPTION

Figure 1:
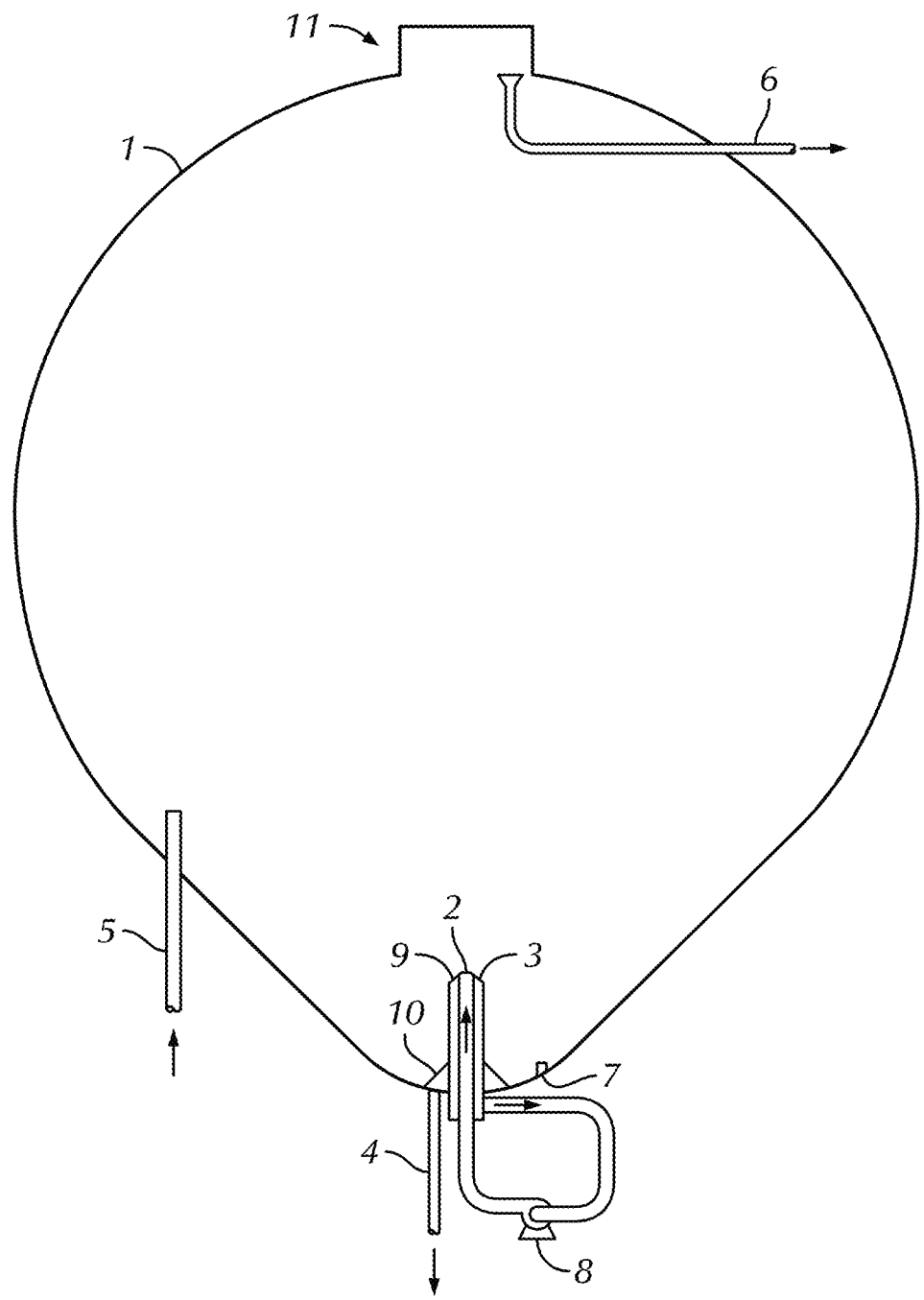
FIG. 1 illustrates an anaerobic sludge digesters having a jet nozzle assembly according to one or more embodiments disclosed herein.

Embodiments disclosed herein relate to systems and processes for anaerobic digestion of biosolids retained in a digester. More particularly, embodiments disclosed herein relate to a process for more efficient mixing of the biosolids circulated through a digester jet nozzle assembly.

The following is directed to various exemplary embodiments of the disclosure. Although one or more of these embodiments may be preferred, the embodiments disclosed should not be interpreted, or otherwise used, as limiting the scope of the disclosure, including the claims. In addition, those having ordinary skill in the art will appreciate that the following description has broad application, and the discussion of any embodiment is meant only to be exemplary of that embodiment, and not intended to suggest that the scope of the disclosure, including the claims, is limited to that embodiment.

Certain terms are used throughout the following description and claims refer to particular features or components. As those having ordinary skill in the art will appreciate, different persons may refer to the same feature or component by different names. This document does not intend to distinguish between components or features that differ in name but not function. The Figures are not necessarily to scale. Certain features and components herein may be shown exaggerated in scale or in somewhat schematic form and some details of conventional elements may not be shown in interest of clarity and conciseness.

In the following discussion and in the claims, the terms "including" and "comprising" are used in an open-ended fashion, and thus should be interpreted to mean "including, but not limited to . . . ." Further, the terms sludge, liquid sludge, sludge mass, and biosolids as used herein are interchangeable.

The following embodiments recognize that current systems are challenged in effectively mixing the sludge contents within the vessel with low equipment, maintenance and operating costs. As used herein, "driving energy" relates to the energy initially supplied by pumps and is directly related to operating cost. Therefore, the following embodiments recognize that methods and apparatuses to provide required mixing performance for a lower driving energy are desirable.

Disclosed herein is a system that utilizes an inlet and outlets for the recirculation system on an Egg-Shaped Digester (ESD) in a vertical arrangement with an optional heavy sediment and inert particle (grit) flush outlet and optional sensor to determine when sediment accumulates. This provides for faster and more complete mixing and a reduction in piping compared to other jet-mixed systems. The optional grit flush outlet system may allow rapid grit or sediment removal and reduces the frequency of a general outage which involves emptying of the entire vessel.

Embodiments herein may provide a better arrangement of recirculation nozzles in an ESD, reducing cost, providing faster mixing, greater particle retention times, reduced Coefficient of Variation (COV) and protection of the pump from erosion caused by grit. A sediment sensor may prevent situations where sediment builds up without the operator's awareness. This will allow for lower operating costs, improved performance and reduced risk while maintaining mixing performance as desired. The optional grit flush outlet offers potential to reduce maintenance cost and lost ESD operation time by decreasing the frequency of required outages for grit removal.

Jet mixers are well known in vessel mixing and have been in use many decades. Jet mixers have also specifically been used in ESD vessels. However known designs utilize multiple inlets and outlets distributed around the ESD. These arrangements require additional piping and are not optimally located with respect to each other for mixing.

Further, a jet mixer with a draft tube has been used, but may be less efficient than other methods because it limits free expansion of the jet, which is the process that entrains and mixes the existing contents of a vessel. Other designs use propellers in draft tubes, which is undesirable due to maintenance of moving parts in the ESD vessel and similarly limits entrainment of fluid and mixing effectiveness.

Due to the location of the recirculation inlet and outlet in designs utilizing draft tubes, regions of low fluid velocity can occur near the bottom of the ESD vessel when the mixing system is in an up-flow mode. This can lead to increased deposition of sediment on the bottom of the vessel, reducing the working volume of the ESD (which in turn reduces the volatile solids retention time) and potentially causing damage to the ESD.

While current systems mount the recirculation outlet high enough to reduce the intake of grit and subsequent erosion of the pump, they typically do so by mounting the outlet on the side of the vessel, which is not ideal for flow.

Embodiments herein recognize the fact that jet mixing depends on the length of the free jet, and that maximizing this length improves mixing.

The addition of a grit removal outlet with sediment sensor may allow for the determination of sediment build up on the bottom of the ESD and enable flushing the sediment before it affects the operation of the ESD.

Mixing arrangements herein provide a high pressure (jet) nozzle (digester inlet) circulating fluid received from one or more low pressure nozzles (digester outlet(s)). The jet nozzle and the low pressure nozzle(s) are arranged to provide for one or more objectives, including: (a) a desirable mixing pattern; (b) an acceptable COV based on the expected digester contents, gas production, and other operating factors known to those skilled in the art; and (c) efficient large solids settling and removal.

Figure 3:
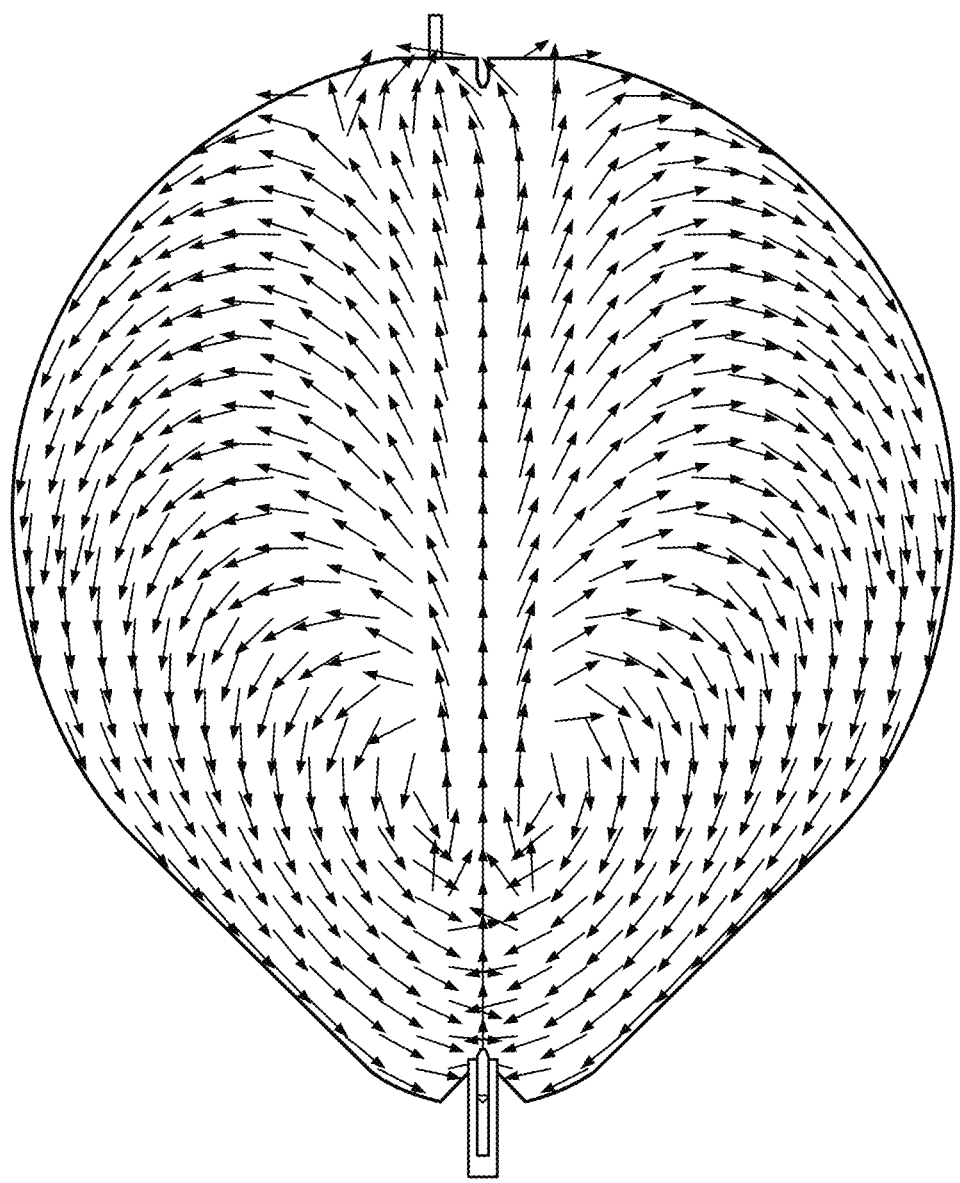
FIG. 3 illustrates a velocity pattern for up flow mode using a center recycle and jet nozzle assembly.
Figure 4:
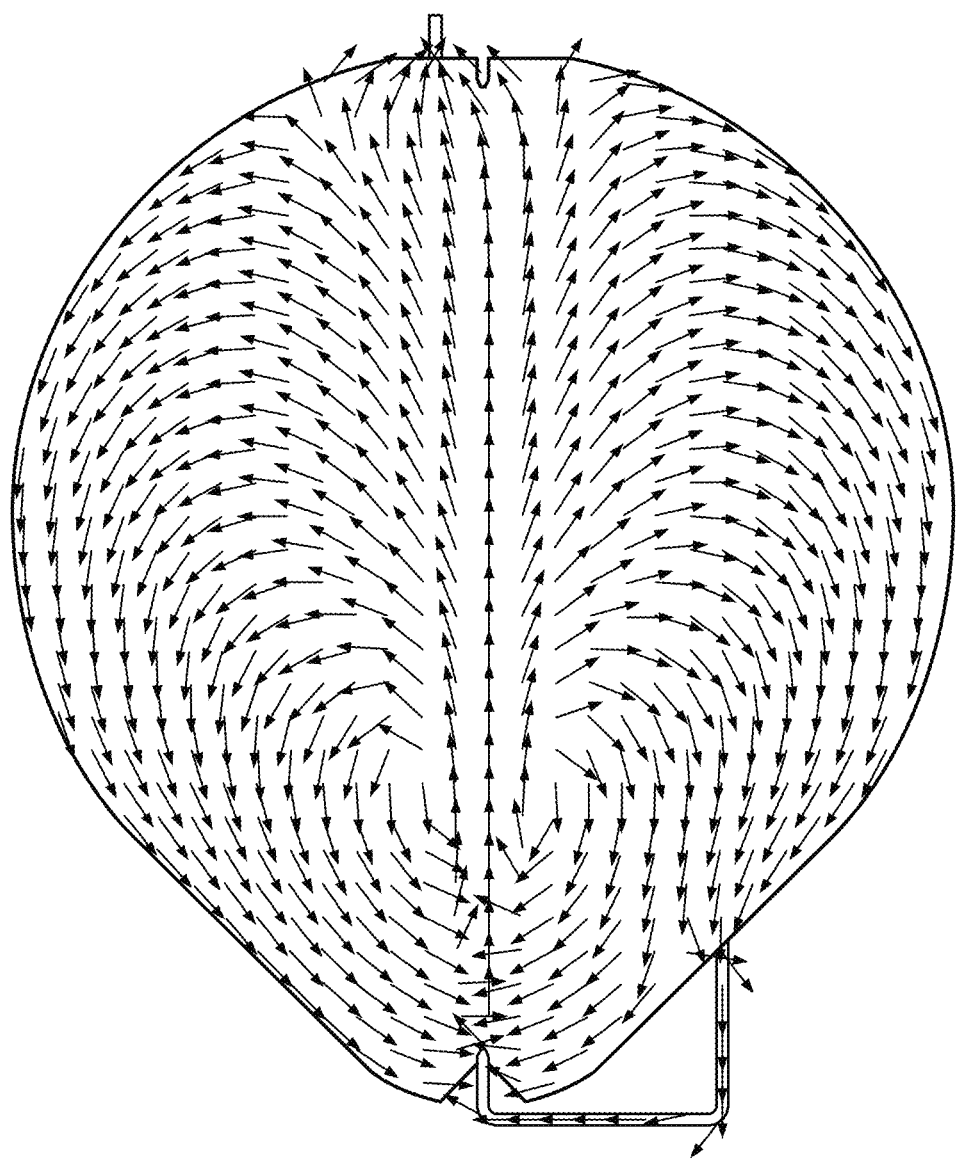
FIG. 4 illustrates a velocity pattern for up flow mode using a side recycle and jet nozzle assembly.

To generate a desirable mixing pattern, the high pressure nozzle and low pressure nozzle(s) are generally located on the same portion of the digester (top area of the ESD, bottom area of the ESD, or both). Further, the low pressure nozzle(s) should be located such that a flow pattern is developed which promotes mixing. For example, a cross-sectional view of a desirable flow pattern may be as shown in FIGS. 3-4, which exhibit two flow loops (up from jet, out to both sides, and down to the low pressure nozzles). In contrast, undesirable location of the jet in relation to the low pressure nozzles may create a singular flow loop, which is not beneficial for mixing.

As noted above, target COV for a given digester may depend upon the feed rates, digestion rates, sludge composition, and microbials used. Some digesters may work with a COV of 30%, while others may not tolerate such a low degree of mixing, and may require a COV of 10% or 15%. While it has been found by the present inventors that a coaxial arrangement of the jet and low pressure outlet(s) may provide the greatest mixing (lowest COV), piping considerations, operator preference, and COV requirements may allow for the jet nozzle to be located a distance from the low pressure nozzle(s) in some embodiments.

To allow for settling of larger solid particles, the jet nozzle may extend into a bottom of the digester vessel a distance, such as 1 to 10 feet or more, depending upon the size of the digester, and may direct the circulating fluids upwards into the digester. A circulation pattern similar to those illustrated in FIGS. 3-4 may result. While desirable to locate the jet nozzle centrally, acceptable flow patterns may result where the jet is located off center, such as within the inner 50% of the radius of the vessel, relative to center, the radius of the vessel being the radius of the digester at the uppermost height of the jet nozzle as discussed below.

The low pressure nozzle(s) may then be located proximate to or concentrically around the jet nozzle so as to promote the "two loop" flow pattern noted above. For example, two, three, four, or more low pressure nozzles may be circumferentially located around the jet nozzle, such as within 40% of the digester radius, such as within 37% of the digester radius, such as within 25% of the digester radius from the jet nozzle, within 15% of the digester radius, or within 10% or 5% of the digester radius.

In one or more embodiments, three or four low pressures nozzles may be located circumferentially around the jet nozzle. Where the low pressure nozzles are disposed a distance from the jet nozzle, the low pressure nozzles may be within a distance of 10 jet nozzle radii from the location jet nozzle. In other embodiments the low pressure nozzles may be located at a distance of less than 3 jet nozzle radii from the jet nozzle.

The location of the jet nozzle and plurality of low pressure nozzles may be dictated by the overall shape and dimensions of the ESD. For example, the jet nozzle may be located at a distance of up to 37% of the radius of the ESD, and have four low pressure nozzles positioned circumferentially at a distance of 3 times the jet nozzle radii from the jet nozzle. In other embodiments, the jet nozzle may be positioned substantially along the centreline of the ESD and have as few as one low pressure nozzle located between 1 and 10 jet nozzle radii from the jet nozzle.

In yet other embodiments, the jet nozzle and low pressure nozzles may have a pipe-in-pipe type arrangement. Such an arrangement may be located at any point where the separate jet nozzle and low pressure nozzles, separately, would be located. Preferably, the concentric pipe-in-pipe arrangement is located centrally within the digester, advantageously utilizing the symmetric shape of the digester to promote a desired flow pattern and sufficient mixing within the vessel.

The jet nozzle and the low pressure nozzle(s) may extend into the vessel the same distance in some embodiments. In other embodiments, the jet nozzle extends further into the digester than the low pressure nozzle(s). The low pressure nozzles may extend a distance into the vessel to allow for a low velocity flow zone proximate the bottom of the vessel, promoting settling of larger solids but maintaining the smaller solids within the circulation and mixing loops. The length for which the jet and low pressure nozzles extend into the vessel may be relatively short, such as 1 or 2 feet, but may be greater so as to avoid plugging or the need for frequent flushing of solids. In some embodiments, the jet nozzle may extend into the vessel up to 5% of the total internal height of the vessel, or up to 10%, up to 15%, up to 20%, or up to 25% of the height in other embodiments.

FIG. 1 illustrates a generally egg-shaped anaerobic sludge digester in combination with a jet nozzle assembly disposed proximate to the bottom of the digester in accordance with embodiments disclosed herein. The terms "vessel" and "digester" may be used herein interchangeably. Digester 1 is a sludge containment vessel useful for containing sludge, whereby naturally occurring anaerobic digestion of the sludge is promoted through optimization of the conditions therein. Digester 1 is characterized by sloping sides creating a conical top section and a conical bottom section, which transition by sloping towards a circular middle section.

Digester 1 includes a sludge inlet 5 which receives raw sludge for digestion. Digester 1 further has a cylindrical gas-collecting top 11 that is useful for collecting the gas emissions of the anaerobic digestion process. Digester 1 illustrates a shape of a vessel useful for performing the embodiments described herein and illustrated in the Figures, although other digester shapes are also contemplated. In some embodiments, the depth of the vessel to the diameter of the vessel may be a value within a range, such as the range of 0.8 to 1.2 times the diameter of the vessel. While the embodiments disclosed herein may be used for digesters of all sizes and volumes, embodiments disclosed herein particularly provide a much needed solution for digesters seeking to use a central jet nozzle assembly located on a center vertical axis for effective mixing of digesters with volumes of at least 120,000 gallons or more. As previously described, existing systems have often struggled to provide optimal mixing and optimal efficiency when implemented with a single jet nozzle or central draft tube intended to mix digesting sludge volumes of 120,000 gallons or more. The process, as disclosed herein, should allow for vessels larger than 120,000 gallons to function at higher efficiency, possibly optimal efficiency.

FIG. 1 shows a jet nozzle assembly located proximate to the bottom of the digester 1. The jet nozzle assembly has a jet nozzle 2 which produces a free jet in up flow mode, thereby effecting mixing within the digester 1. The pump draws sludge into the recirculation system through a plurality of low pressure nozzles 3 arranged concentrically around the jet nozzle 2. As illustrated, the jet nozzle is located approximately along a centerline of the ESD with the low pressure nozzles located circumferentially around the jet nozzle, however, as described above, the jet nozzle and low pressure nozzles may be located in any position as necessary by the overall dimensions of the ESD. The pressure used to generate the free jet from jet nozzle 2 is generated by recirculation pump 8. Recirculation pump 8 may be located externally to the digester 1. In one or more embodiments, the jet nozzle assembly may be equipped with stiffeners 9 and supports 10. The placement of these stiffeners may allow for structural rigidity of the jet nozzle assembly during turbulent flow within the digester 1. Digester 1 may be equipped with a digested sludge drain 6 which may help eliminate the development of foam.

Recirculation pump 8 acts as a pump useful in mixing the contents of digester 1, and directing the sludge through the piping system. In the illustrated embodiment, recirculation pump 8 is located externally to an outer wall of digester 1 so as to reduce any operational failure that may result from locating recirculating pump 8 within the somewhat harsh environment of digester 1. Nevertheless, in some embodiments, recirculation pump 8 may be included within an interior of digester 1, including being provided with a protective housing for preventing retained sludge from affecting the operation of recirculation pump 8.

Recirculation pump 8, when activated, acts to draw in sludge through the plurality of low pressure nozzles 3. Additionally, recirculation pump 8 may provide the necessary sludge flow volume and pressure head to drive the outlet jet nozzle 2 and create the necessary free jet within the digester 1.

FIG. 1 also illustrates a sediment removal assembly 4, which may include one or more pipes useful in collecting and routing sediment out of digester 1. The sediment removal assembly 4 may be activated by the sediment level sensor 7. The sediment level sensor 7 may be located low enough such that sediment does not enter low pressure nozzles 3, yet high enough to allow for some buildup of sediment while not constantly activating the sensor at a level of minimal buildup. The amount of sediment buildup may vary from installation to installation, and may vary due to operator preference. The flow in sediment removal assembly 4 may be reversed to allow back-washing of the assembly.

Conventional ESDs, which use draft tubes, call for periodic and frequent reversal of flow in the draft tube to optimize the distribution of light floatable solids and heavy settling solids in the main body of the digester. As disclosed herein, the jet nozzle assembly does not require flow reversal in order to maintain mixing with the digester 1. However, if flow reversal is desired, a similar jet nozzle assembly, operating in downflow, may be disposed proximate to the top of the ESD to direct the free jet downward while drawing in sludge horizontally. Additionally, embodiments operating only in downflow are contemplated herein.

Figure 2:
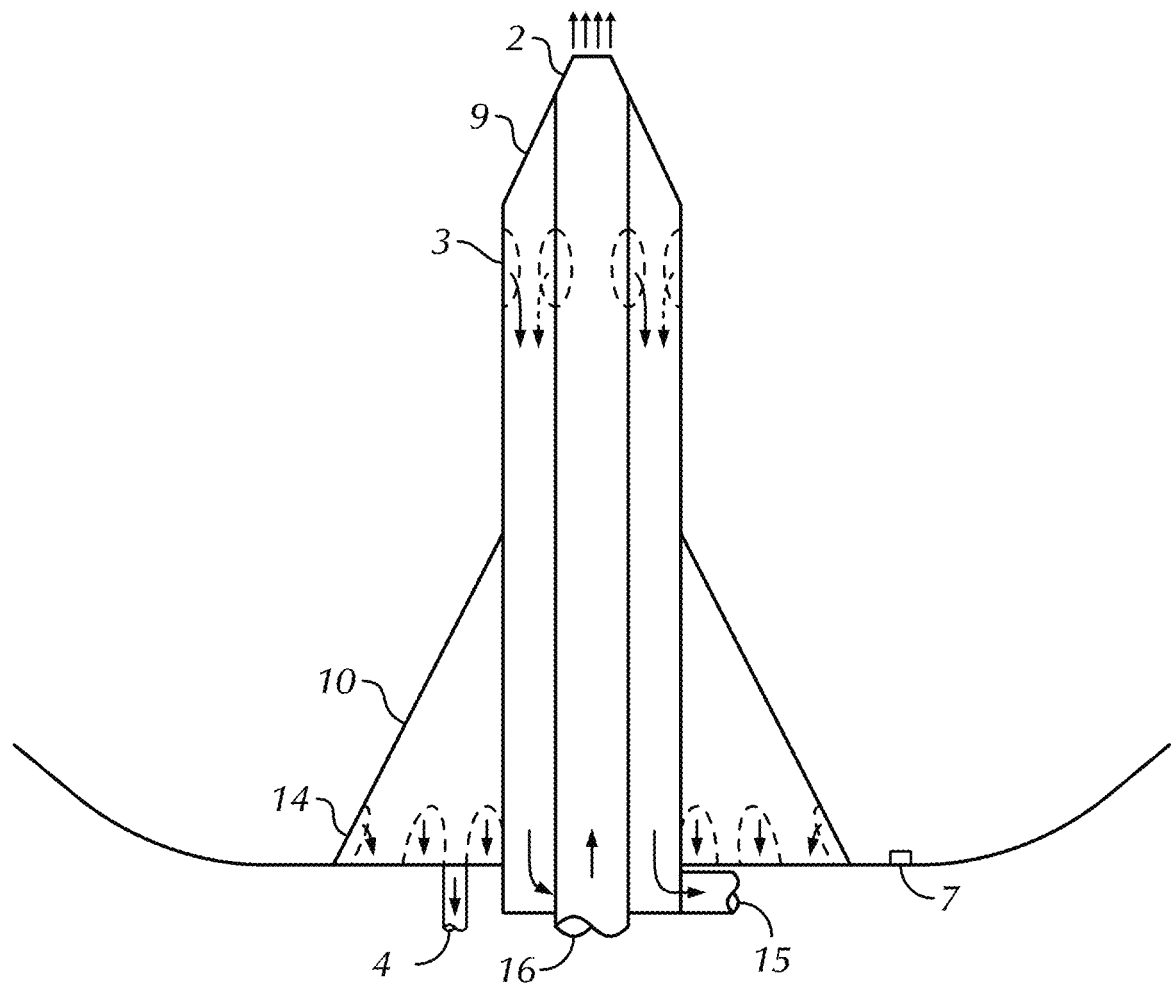
FIG. 2 illustrates a jet nozzle assembly according to one or more embodiments disclosed herein.

FIG. 2 illustrates a cross section of an embodiment of the jet nozzle assembly in greater detail. As illustrated, the jet nozzle and low pressure nozzles are in a tube-in-tube arrangement, however any arrangement described above is contemplated herein. Also, as illustrated, sludge is drawn through a plurality of low pressure nozzles 3 and through a recirculation system 15. The sludge is pumped using the recirculation pump 8, not illustrated, and travels through recirculation outlet 16 and through jet nozzle 2, producing the free jet and mixing the sludge within the digester 1. The overall height of the jet nozzle assembly may be from 1 to 10 feet in height, depending on the mixing requirements, and overall digester shape. A central pipe may terminate in the jet nozzle 2, while the plurality of low pressure nozzles 3 are disposed on an outer pipe which is located circumferentially around the central pipe. The outer pipe and plurality of low pressure nozzles form a low pressure nozzle assembly. The low pressure nozzle assembly forms a cylindrical wall where the plurality of low pressure nozzles 3 may be openings in the cylindrical wall, such as square, oval, circular or other shaped openings in the cylindrical wall.

In some embodiments, sediment ports 14 may be used to aid in directing the sediment to sediment removal assembly 4. Sediment ports 14 may prevent sediment from building up around the jet nozzle assembly, blocking low pressure nozzles 3. As illustrated, supports 10 may be a conical support. In one or more embodiments, supports 10 may be fins. Support 10 may also have one or more sediment ports. Depending on the requirements of the ESD and sediment build up rates, each support 10 may be equipped with 0 to 5, or more, sediment ports. Such ports may also vary in size from 1 inch, to 10 inches or greater depending on the sediment particle diameter and sediment build up rate. The sediment ports 14, while illustrated proximate to the bottom of the supports 10, may have a diameter of 4 to 8 inches, may be placed at a desired height up the support 10, and may also be placed in two or more rows, vertically, as necessary to aid in sediment removal.

In one or more embodiments, the sediment removal assembly 4 may be located near the bottom of the digester and may remove sediment through a sediment outlet.

In one or more embodiments, the sediment level sensor 7 is located near the bottom of the vessel, but above a height of sediment build up, and below a height of the low pressure nozzle assembly openings. A control system may control the sediment removal assembly and may activate the sediment outlet to remove sediment when the height of sediment buildup reaches a height where the sediment level sensor is activated. This height may be a predetermined height below the sediment level sensor 7, or may be at a height of the sediment level sensor 7. Alternatively, level sensor 7 may trigger an alarm and an operator may manually empty sediment from the vessel.

In some embodiments, the jet nozzle 2 may receive up to 100% of recirculation pump 8 discharge. In order to provide sufficient momentum for mixing, the jet nozzle 2 may have a diameter of 2 to 10 inches. In some embodiments the jet nozzle may be 6 inches in diameter. The jet nozzle assembly should be placed at a height above the plurality of low pressure nozzles 3 to ensure proper mixing and prevent flow directly between the jet nozzle and low pressure nozzles. The height differential between the jet nozzle 2 and plurality of low pressure nozzles 3 may a minimum of 2 inches. The plurality of low pressure nozzles 3 also have an axial distance from the jet nozzle 2. Such an axial distance may be 2 to 6 times the outer diameter of the jet nozzle. The jet nozzle 2 and plurality of low pressure nozzles 3 may be positioned in such a way so as to allow the jet nozzle to be off-center with respect to the centerline of the ESD, and/or with respect to the low pressure nozzles 3.

In one or more embodiments disclosed herein, the plurality of low pressure nozzles 3 may be circular in shape, and may have a diameter of 1 to 8 inches. In one or more embodiments the diameter of the plurality of low pressure nozzles 3 may be 2 to 7 inches, or greater than 4 inches. The diameter of each of the plurality of low pressure nozzles 3 may not be equivalent in size. In should be noted that any number of low pressure nozzles may be used, depending on desired flow, overall mixing, and overall digester shape. Additionally, the plurality of low pressure nozzles 3 may have an oval shape. In embodiments oval nozzles are used, the major diameter may be from 1 to 8 inches, while the minor diameter may be from 1 to 7 inches.

Advantageously, the jet nozzle assembly may increase the mixing of sludge moving through the digester, partly because the jet nozzle 2 forms a free jet in upflow approximately the height of the digester, and low pressure nozzles 3 draw sludge proximate to the bottom of the vessel, but above the sediment. As seen in FIGS. 1 and 2, and described above, the jet nozzle assembly is disposed proximate to a center of the digester. However, other configurations are also contemplated. For example, the jet nozzle may be located at a distance of 25% of the ESD diameter from the centerline of the ESD, and one or more low pressure nozzles may be located at a predetermined distance from the jet nozzle, rather than as a pipe-in-pipe configuration.

In one or more embodiments, the plurality of low pressure nozzles 3 may be located proximate to the side of the digester 1 instead of concentrically around the outlet jet nozzles, and the jet nozzle 2 may be located to the side of digester 1 instead of at the center of the vessel. The jet nozzle 2 and low pressure nozzles 3 may be located within one quarter of the vessel radius of the center of the vessel. In this configuration, supports, sediment removal assemblies, and sediment level sensors may still be used. The position of the level sensor, for example, may be proximate to the bottom of the vessel, above the level of sediment, and still below the height of the plurality of low pressure nozzles. Additionally, a single low pressure nozzle 3 may be used instead of a plurality of low pressure nozzles 3. In one or more embodiments, the single low pressure nozzle 3 may be located 2 to 6 inches to one side of the jet nozzle 3.

While illustrated as concentric, low pressure nozzles 3 may be disposed a small distance from the jet nozzle 2, as described above. The distance may depend on the overall shape of the vessel, but should be arranged to prevent "short circuiting" of the flow. "Short circuiting" as described herein is when a close proximity of the inlet and outlet cause flow to substantially travel directly between the outlet and inlet, thereby reducing overall mixing. It has been found that when the jet nozzle 2, and low pressure nozzles 3, are in a proximate location, overall mixing in the digester is increased. However, in one or more embodiments, it may be advantageous to locate the low pressure nozzles a greater distance from the jet nozzle depending on the overall shape and dimensions of the ESD as well as heavy sedimentation rate.

As illustrated, having the low pressure nozzles 3 placed concentrically around jet nozzle 2 may provide a single assembly which exhibits better overall mixing within the digester. The outer pipe containing the plurality of low pressure nozzles 3 may be of a diameter which is 2 to 5 times the outer diameter of the jet nozzle 2. This may ensure sufficient flow to the recirculation pump 8. Further, the low pressure nozzles 3 may have a substantially horizontal entry into the jet nozzle assembly. Depending on the desired mixing and overall vessel shape, the plurality low pressure nozzles 3 may have an inlet direction that directs the flow of fluid from above, or below, the low pressure nozzle height. Embodiments where each of the plurality of low pressure nozzles 3 have a different entry orientation are also contemplated herein.

It is envisioned that larger digesters with large volumes of retained sludge may operate with a single jet nozzle assembly and still achieve optimum or near optimum efficiency and mixing without the need for additional circulation pumps. It is intended that this system as illustrated in FIGS. 1 and 2 may be operable on large digesters, whereby a large digester may be generally described as a digester with liquid sludge volumes of 120,000 gallons to 3,000,000 gallons of volume or more. Providing a more efficient and cost-effective system for moving sludge through larger digesters is highly desirable. Larger digesters can handle a higher amount of sludge volume as compared to smaller digesters, and thus can produce a greater amount of gas collectible in the gas collecting dome portion of the digester, which is a benefit of using larger digesters. As previously discussed, this emitted biogas is much needed as natural fuel source in addition to being needed for various other useful purposes. Up until now, the pumping requirements for moving significant quantities of sludge between the top, middle, and bottom sections of large digesters has been a limiting factor on the size of digesters using a single central draft tube mixing arrangement. The proposed embodiments herein may provide a better alternative for large digesters to mix the contents therein using a jet nozzle assembly and single circulation pump as illustrated in FIGS. 1 and 2.

In one or more embodiments herein, the jet nozzle assembly may be in a pipe-in-pipe type assembly. The outer pipe may include the plurality of low pressure nozzles 3, forming the low pressure nozzles assembly. Stiffeners 9 may form the upper portion of a cone attaching to the central pipe, with the plurality of low pressure nozzles 3 being located on the vertical portion of the assembly. In other embodiments, the outer pipe containing the plurality of low pressure nozzles 3 may have a flat upper portion, or horizontal wall, that connects at substantially 90 degree angles with the inner pipe containing the outlet jet nozzle 2. Additionally, the stiffeners 9 may be a flat or round bar connecting the outer wall of the outer pipe with the outer wall of the inner pipe, thereby providing support for the assembly.

In embodiments where a cone shaped upper portion is used, the plurality of low pressure nozzles 3 may be located on the cone shaped upper portion, rather than the vertical portion of the assembly. Alternatively, in embodiments where a flat upper portion is used, with or without the flat or round bars, the plurality of low pressure nozzles may be located on the horizontal top portion of the outer pipe.

Referring again to FIG. 2, in one or more embodiments, supports 10 may be a height of between 0.2 and 0.8 times the overall height of the jet nozzles assembly, while the bottom width may be 2 to 5 times the outer diameter of the low pressure nozzle assembly and slope generally toward to the low pressure nozzle assembly. In one or more embodiments, supports 10 may be fin shaped and placed concentrically around the jet nozzle assembly, providing lateral support within the digester. Supports 10 may also have a curved outer edge, or may be substantially rectangular. In one or more embodiments, four fin-shaped supports 10 may be placed at 90 degree angles from each other. In other embodiments, 1 to 8, or more, supports may be used and placed at angles as necessitated by the overall digester shape. In one or more embodiments, one or more supports 10 may be a different shape than the other supports, and the supports may be generally disposed on one side of the jet nozzle assembly, for example, opposite the sediment level sensor 7.

In one or more embodiments disclosed herein, is a process for operating the system as described in FIGS. 1 and 2. Sludge is fed into the digester 10 via the sludge inlet 5. The sludge is drawn into the recirculation system through the one or more openings in the low pressure nozzle assembly, through the plurality of openings 3. The recirculation pump 8 pressurizes the sludge and the pressurized sludge is ejected through the jet nozzle 2 into the digester system. This pressurized ejection forms the free jet within the digester system, facilitating the mixing of the sludge in the digester system.

The process may be operated in an up flow mode when the jet nozzle assembly is disposed proximate to a bottom of the vessel, in a down flow mode when the jet nozzle assembly is disposed proximate to a bottom of the vessel. Additionally, the process may be operated in alternating up flow and down flow modes when a first jet nozzle assembly is disposed proximate to the bottom of the vessel and a second jet nozzle assembly is disposed proximate to the top of the vessel.

The level of sediment in the digester system may be monitored using the sediment level sensor 7. When the sediment level sensor 7 activates, a controller may activate the sediment removal assembly and sediment may be removed from the bottom of the digester system through a sediment removal assembly 4.

EXAMPLES

Example 1

Figure 5:
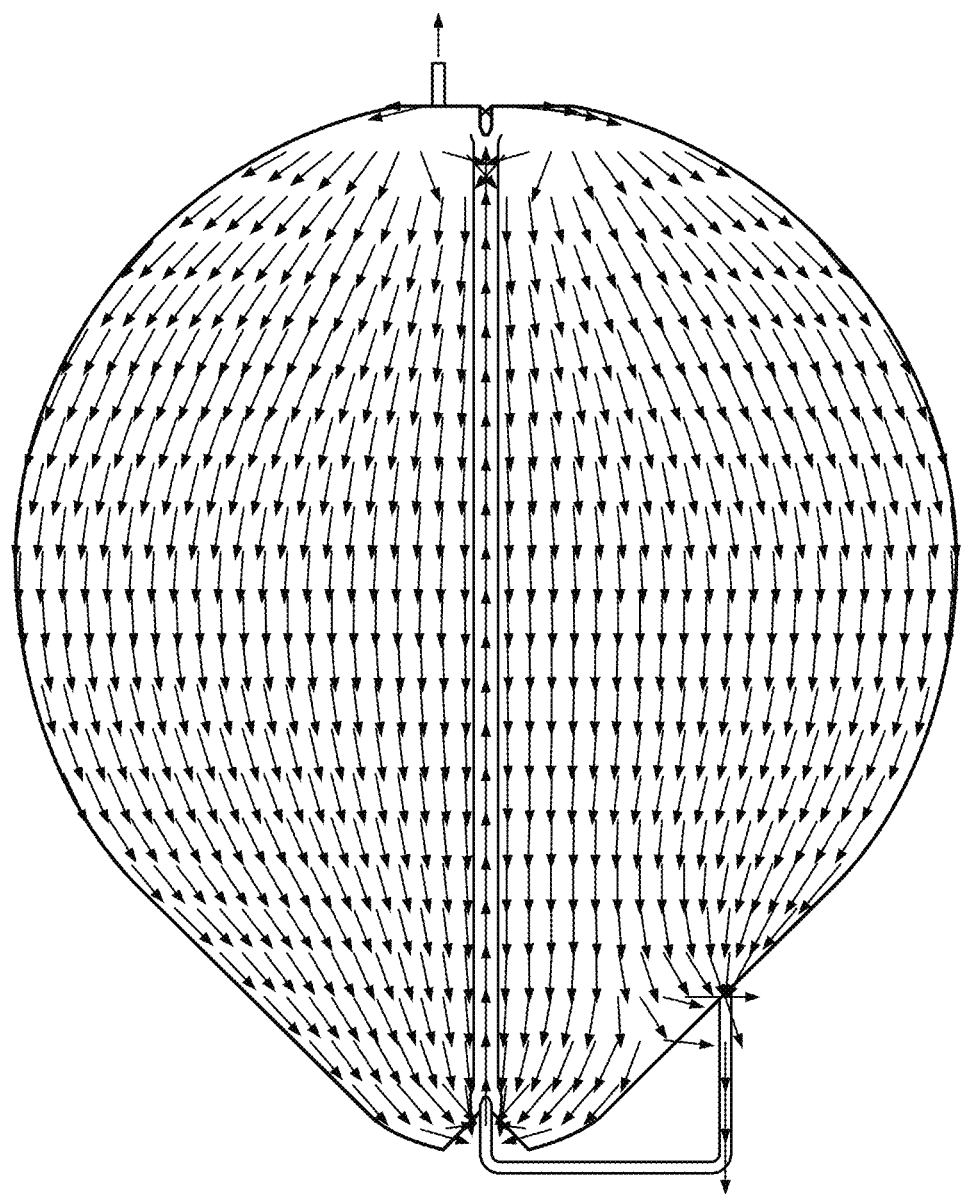
FIG. 5 illustrates a velocity pattern for an ESD with a conventional draft tube.

FIGS. 3, 4 and 5 illustrate velocity and flow patterns at a cross section through the center of the ESD vessel simulated using computational fluid dynamics analysis. Each simulation was performed at the same flowrate and driving energy through the recirculation pump 8, with only the mixing system design varying. FIGS. 3 and 4 illustrate simulated velocity patterns and flow patterns according to embodiments disclosed herein. Computational fluid dynamics modelling shows that embodiments herein provides more complete mixing, as measured by a lower coefficient of variation within the ESD, compared to designs using a draft tube. Due to the improved COV, the volatile solids retention time is increased, allowing for better volatile solids reduction. The placement of the recirculation outlet next to or concentric with the outlet allows for faster mixing, as measured by the number of hours required to reach the minimum COV.

FIG. 3 illustrates a velocity pattern associated with the jet nozzle according to one or more embodiments disclosed herein. In FIG. 3, the velocity pattern is illustrated with respect to one or more embodiments where the plurality of low pressure nozzles are located concentrically around the jet nozzle. As seen, in this configuration the free jet would expand as it travels the height of the ESD, moving substantially all of the contents of the vessel for effective mixing. There would be no areas of low or no flow along the walls that allow buildup of sediment.

FIG. 4 illustrates the velocity pattern associated with the jet nozzle according to one or more embodiments disclosed herein. In FIG. 4, the velocity pattern is illustrated with respect to one or more embodiments where the plurality of low pressure nozzles are located proximate to the side of the digester and away from the jet nozzle. As seen, in this configuration the free jet would also be able to expand as it travels the height of the ESD and to move substantially all of the contents of the vessel for effective mixing. As seen in this embodiment, flow would have a higher propensity for being directed to the side of the digester with the low pressure nozzles and there would be an area of low velocity flow along the vessel wall between the jet nozzle and low pressure nozzle. This configuration may have a greater propensity for sediment buildup than the configuration of FIG. 3, but there would still be sufficient flow to ensure complete, or near complete, mixing of the contents of the digester.

The above described systems of FIGS. 3 and 4 would provide a more suitable environment for anaerobic digestion processes to occur within a digester as mixing by means of flow entrainment would be more efficiently achieved using the above-described systems. The jet nozzle assembly as disclosed herein should successfully help overcome factors that reduce the mixing of sludge transported using draft tubes, such as without limitation, conventional flow head loss, static head loss, pipe friction, turbulence in the mixing zones, foam and froth accumulated on the surface of sludge, and the viscosity of the sludge.

Accordingly, the illustrated in FIGS. 3 and 4 would operate according to the same principle, whereby the flow rate in the digester is made up of the flow from the jet nozzle and the flow would be entrained from the surrounding liquid. The high velocity discharge of the jet nozzles positioned at the bottom of the digester would entrain greater volumes of sludge. The entrained flow would be mixed primarily through turbulent flow mechanisms, which advantageously assists in achieving predicted levels of efficiency for a mixing system that uses a single centrally located jet nozzle assembly.

FIG. 5 illustrates the velocity pattern of an ESD with a conventional draft tube assembly. As seen, in this configuration the majority of the fluid velocity and fluid flow occurs within the draft tube. The only locations for entrainment into the jet are between the nozzle and the bottom of the draft tube and between the top of the draft tube and the top surface of the vessel contents. The flow exiting the draft tube impinges on the top surface, loosing momentum. The flow in the remainder of the vessel is slow, which may allow sediment buildup of biosolids to occur. As seen, the use of a draft tube may limit the flow entrainment necessary to efficiently mix the contents of the digester and may allow sediment buildup, reducing the active volume of the digester.

The steady-state COV was calculated for each of the analyses illustrated in FIGS. 3-5. A lower COV is better, with 0% representing perfect mixing. The COV and mixing time may be reduced by increasing the recirculation pump flowrate, and thus the driving energy in the vessel. These analyses model the same flowrate to provide a relative comparison of mixing system designs. The location of the jet nozzle and low pressure nozzles may be determined by the maximum desired COV.

The draft tube design illustrated in FIG. 5 reaches a minimum COV of 24%. The designs illustrated in FIGS. 3 and 4 would reach a minimum COV of 13%, which is an 84% improvement of mixing. Embodiments disclosed herein would reach that COV in 9.9 hours while the existing draft tube designs reach the minimum COV in 11.1 hours, which corresponds to an 11% reduction in mixing time. Accordingly, ESDs using a center jet nozzle design would offer marked improvement over draft tube designs.

The mean residence time (MRT) was calculated for each of the analyses illustrated in FIGS. 3-5. The MRT is a measure of how long on average volatile solids stay in the ESD before being removed by the digested sludge drain. A longer MRT corresponds to greater volatile solids reduction.

The typical calculation for the MRT value assumes perfect mixing and is therefore determined indirectly from a mass balance comparing the raw sludge inlet flowrate to the ESD volume. To compare different mixing systems with imperfect mixing computational fluid dynamics analysis is used. In the analysis it is measured by injecting particles into the raw sludge inlet and measuring how much time it takes for each particle to leave the digested sludge drain. The mean of these measurements is then calculated.

The MRT for the draft tube design illustrated in FIG. 5 is 23 days. The MRT for embodiments disclosed herein using side recycle and center recycle would be 25.4 and 25.5 days respectively. Accordingly, the jet nozzle assembly disclosed herein would provide improvement for the digestion of sludge over existing designs.

Example 2

The performance of a jet-mixer system, which may be quantified by COV, is related to the location at which the system is installed in the ESD, and the spatial orientation to the ESD vessel centreline.

A model was used to determine how offsets of the coaxial nozzle assembly from the vessel centerline affect mixing performance and how symmetrical offsets separating the high pressure nozzle from the low pressure nozzle affect mixing performance. The mixing performance is quantified by calculating the coefficient of variation (COV) from a CFD analysis, where a lower COV indicates a more-homogeneous mixture. A tracer representing sludge is introduced at the ESD inlet pipe and the COV is calculated from the tracer concentration over time. The COV will eventually reach a steady-state value. The steady-state COV, the time to reach steady state, and the rate of mixing over time all depend on the nozzle arrangement and jet momentum.

In order to compare performance of each nozzle arrangement, a baseline was established as a performance metric. The baseline configuration was taken as the coaxial nozzle arrangement located at the vessel centerline. This reaches a steady-state COV of 13.4% after 30,000 s (8.3 hr). The mixing performance metric is defined as the COV of each nozzle arrangement at the same time of 30,000s normalized by the baseline COV.

As illustrated by FIGS. 6A, 6B, 6C, and 6D, the model was performed using different offsets. The nozzle offsets are defined as a fraction of the vessel radius R. The offsets were chosen to bound the distance where there is a clear divergence in mixing performance. For the coaxial nozzle arrangement offsets of 0.00 R (illustrated in FIG. 6A), 0.37 R (illustrated in FIG. 6B), 0.45 R (illustrated in FIG. 6C), and 0.75 R (illustrated in FIG. 6D) were studied. Additionally, symmetrical nozzle arrangement offsets of ±0.37 R, ±0.45 R and ±0.75 R were studied. All were compared to the baseline arrangement with 0.00 R offset.

The model showed that COV was almost unchanged for 0.37 R offset, illustrating that offsets from 0.00 R to 0.37 R behave similarly. At 0.75 R, the coaxial nozzle arrangement had a COV 1.6 times the baseline (a COV of 21%). The symmetric nozzle arrangement had a COV 3.9 times the baseline (a COV of 51.7%). For both studies the offset where the COV shifts from acceptable to unacceptable performance was between 0.37 R and 0.45 R.

The results of the modelling indicated that a coaxial arrangement at the vessel centerline may be the preferred location of the nozzles. Separating the nozzles by offsetting them symmetrically has a stronger adverse effect on mixing than offsetting the coaxial nozzle arrangement. This finding is contrary to many examples in vessel mixing where the nozzles are separated to prevent short-circuiting.

According to the modelling of COV versus time, the offset should be kept to about 0.37 R, or less, for optimal mixing.

In terms of fabrication and assembly, the jet nozzle assembly can be fabricated as a single unit off site and transported to the construction site. Thus allowing for the jet nozzle assembly to be used for new construction, or retrofitting an existing installation.

One or more embodiments disclosed herein may be used in an ESD, but could be used in any vessel containing suspended solids and requiring mixing.

The low pressure nozzles and jet nozzle may be located close to each other, such as concentric with the jet nozzle in the center, but other arrangements are possible such as parallel pipes where the jet nozzle pipe and one or more low pressure nozzle pipes are separated from the vessel centerline by no more than 37% of the vessel radius respectively. The jet nozzle pipe should always extend past the low pressure nozzle assembly to prevent pulling flow directly from the outlet to the inlet. The low pressure nozzle should be located a distance above the bottom of the vessel that is high enough to reduce entrainment of particles of hard materials, or grit, such as sand. This height is variable and should be set accounting for the density and size of the predominant sources of grit for a particular ESD.

Alternatively, the low pressure nozzles and jet nozzle could be located at the top of the ESD, producing a downwards flowing jet.

Alternatively, an ESD could be configured with a jet nozzle assembly at the bottom and a jet nozzle assembly at the top, and valves configured such that the ESD could be operated in either an up-flow or down-flow mode.

The sediment removal assembly can be located at the bottom of the vessel without the jet nozzle assembly.

If sediment is not present, the sediment removal assembly can be eliminated and the jet nozzle assembly can be lowered if desired.

The low pressure nozzles can be connected to the jet nozzle by means of a stiffener in the form of a conical plate with openings to admit flow. These openings must be large enough so as to not clog with materials that can be present in the vessel. The use of this conical plate can be beneficial to increase the stiffness of the low pressure nozzles and jet nozzle and reduce flow induced vibrations. Alternatively, the conical plate can be eliminated if this stiffening is not needed, or it can be retained in a different form, such as a flat annular plate with openings or radial bars.

The recirculation outlet stiffener may help to support the recirculation pipes and to direct flow in the vessel. This stiffener can be eliminated or serve the same function in a different shape, such as a curved plate tangent with the bottom of the vessel and the recirculation outlet pipe. It is also possible to support the recirculation pipes without providing a flow function, such as using bars between the recirculation pipes and the vessel bottom.

The sediment sensor can signal the operator to manually operate the flush valve or be combined with a control system to automate flushing.

Compared to systems with draft tubes and system with multiple nozzles, the current invention offers a significant cost reduction due to the simplicity of piping and piping supports.

If the COV and solids retention time for an existing design are sufficient, embodiments disclosed herein may allow for achieving the same mixing performance with a lower flowrate, and therefore a smaller pump with reduced operating costs.

The position of the recirculation outlet improves mixing speed by providing a better flow pattern in the ESD. By locating the recirculation outlet high enough above the vessel bottom it minimizes erosion of the pump from grit intake without hindering mixing.

By proper selection of the jet nozzle velocity and flowrate, and with the good flow pattern, deposition of volatile solids as sediment on the bottom of the ESD may be minimized while heavy particles of grit, such as sand, can be deposited on the bottom of the ESD for removal by the sediment removal assembly so as to avoid accelerated wear on the recirculation pump.

The anaerobic process is a complex multi-step symbiotic biological process. Steady liquid temperatures, continuous steady raw sludge feed, and a thoroughly mixed digesting mass substantially improves the process performance, stability, and reliability. The above embodiments describe a system which allows for more effective mixing of sludge retained in a digester. The above embodiments also describe a system that facilitates heat exchange internal to a digester with ongoing mixing within the inner structure of a digester.

While the disclosure includes a limited number of embodiments, those skilled in the art, having benefit of this disclosure, will appreciate that other embodiments may be devised which do not depart from the scope of the present disclosure. Accordingly, the scope should be limited only by the attached claims.

The invention claimed is:

1. A jet nozzle assembly for mixing contents of a vessel, the jet nozzle assembly comprising:
a central pipe terminating at a jet nozzle;
a low pressure nozzle assembly disposed concentrically about the central pipe, the low pressure nozzle comprising a plurality of openings disposed circumferentially about the low pressure nozzle assembly, a cylindrical wall, and a conical wall section connecting a top of the cylindrical wall to the central pipe, and wherein the plurality of openings comprise circular openings in the conical wall;
wherein the plurality of openings are an axial distance from the outlet jet nozzle.

2. The jet nozzle assembly of claim 1, wherein the plurality of circular openings each have a diameter of at least 2 inches.

3. The jet nozzle assembly of claim 1, further comprising one or more supports disposed around the low pressure nozzle assembly, a top of the one or more supports connected to the low pressure nozzle assembly below the plurality of openings, and a bottom of the one or more supports connected to the vessel.

4. The jet nozzle assembly of claim 3, wherein the one or more supports comprises a support skirt having two or more openings proximate a bottom of the support.

5. The jet nozzle assembly of claim 3, wherein the one or more supports a height of between 0.2 and 0.8 times the overall height of the jet nozzles assembly and a bottom width of 1 to 5 times the outer diameter of the low pressure nozzle assembly.

6. The jet nozzle assembly of claim 3, where the one or more supports are fin shaped, have curved outer edge, or are rectangular in shape.

7. A digester system comprising;
a vessel;
a jet nozzle assembly disposed proximate to a top of the vessel, a bottom of the vessel, or both, the jet nozzle assembly comprising:
a central pipe terminating at a jet nozzle;
a low pressure nozzle assembly disposed concentrically about the central pipe, the low pressure nozzle comprising a plurality of openings disposed circumferentially about the low pressure nozzle assembly and a conical wall connecting the top of the cylindrical wall to the central pipe below the jet nozzle;
wherein the plurality of openings are an axial distance from the outlet jet nozzle;
a pump associated with the jet nozzle assembly for circulating fluid from the low pressure nozzles to the jet nozzle and mix contents within the vessel.

8. The system of claim 7, wherein the low pressure nozzle assembly comprises a cylindrical wall, and wherein the plurality of openings comprise circular openings in the cylindrical wall.

9. The system of claim 8, wherein the low pressure nozzle assembly further comprising a horizontal wall connecting the top of the cylindrical wall to the central pipe below the jet nozzle.

10. The system of claim 8, wherein the low pressure nozzle assembly further comprising a flat or rounded bar connecting the top of the cylindrical wall to the central pipe below the jet nozzle and above the point where the cylindrical wall connects.

11. The system of claim 7 further comprising a sediment removal assembly proximate to the bottom of the vessel configured for removal of sediment through a sediment outlet.

12. The system of claim 11 further comprising a sediment level sensor.

13. The system of claim 12, where the sediment level sensor is located proximate to the bottom of the vessel, above a height of sediment build up, and below a height of the low pressure nozzle assembly openings.

14. The system of claim 13, further comprising a control system configure for controlling the sediment removal assembly, wherein the sediment level sensor activates the sediment outlet when the height of the sediment buildup activates the sediment level sensor.

15. The system of claim 7, wherein the jet nozzle is located between 0.00R and 0.37R from the center of the vessel, where R is a radius of the vessel.

16. A process for operating a digester system comprising;
feeding sludge into a vessel via a sludge inlet;
drawing sludge into a recirculation system through one or more openings in a low pressure nozzle assembly;
pressurizing the drawn sludge via a recirculation pump;
ejecting the pressurized sludge through a jet nozzle into the digester system;
forming a free jet within the digester system;
mixing the sludge in the digester system via the free jet;
monitoring a level of sediment in the digester system using a sediment level sensor; and
removing sediment from a bottom of the digester system through a sediment removal assembly;
wherein the low pressure nozzle assembly is disposed circumferentially around the jet nozzle, forming a jet nozzle assembly.

17. The process of claim 16, further comprising operating the jet nozzle assembly in an up flow mode when the jet nozzle assembly is disposed proximate to a bottom of the vessel.

18. The process of claim 16, further comprising operating the jet nozzle assembly in a down flow mode when the jet nozzle assembly is disposed proximate to a top of the vessel.

19. The process of claim 16, further comprising operating the jet nozzle assembly in alternating up flow and down flow modes when a first jet nozzle assembly is disposed proximate to the bottom of the vessel and a second jet nozzle assembly is disposed proximate to the top of the vessel.

20. The process of claim 16, further comprising controlling the sediment removal assembly using the sediment level sensor.

21. A jet nozzle assembly for mixing contents of a vessel, the jet nozzle assembly comprising:
a central pipe terminating at a jet nozzle;
a low pressure nozzle assembly having one or more openings disposed on the low pressure nozzle assembly;
the low pressure nozzle assembly comprises a cylindrical wall and a conical wall section connecting a top of the cylindrical wall to the central pipe, wherein the one or more openings comprise circular openings in the conical wall.

22. The jet nozzle assembly of claim 21, wherein the low pressure nozzle assembly is located concentrically around the central pipe.

23. The jet nozzle assembly of claim 21, wherein the low pressure nozzle assembly is located adjacent to the central pipe.

24. The jet nozzle assembly of claim 21, wherein the low pressure nozzle assembly is located proximate to the center of the vessel.

25. The jet nozzle assembly of claim 21, wherein the low pressure nozzle assembly is located between 0.00R and 0.37R from the center of the vessel, where R is a radius of the vessel.

* * * * *